(12) United States Patent
Leivers et al.

(10) Patent No.: US 9,265,744 B2
(45) Date of Patent: Feb. 23, 2016

(54) FULVIC ACID AND ANTIBIOTIC COMBINATION FOR THE INHIBITION OR TREATMENT OF MULTI-DRUG RESISTANT BACTERIA

(71) Applicants: Stephen William Leivers, Wymondham (GB); Peter Warn, Worsley (GB)

(72) Inventors: Stephen William Leivers, Wymondham (GB); Peter Warn, Worsley (GB)

(73) Assignee: NATRACINE UK LIMITED, Cheshire (GB)

( * ) Notice: Subject to any disclaimer, the term of this patent is extended or adjusted under 35 U.S.C. 154(b) by 0 days.

(21) Appl. No.: 14/383,429

(22) PCT Filed: Mar. 6, 2013

(86) PCT No.: PCT/IB2013/051772
§ 371 (c)(1),
(2) Date: Sep. 5, 2014

(87) PCT Pub. No.: WO2013/132444
PCT Pub. Date: Sep. 12, 2013

(65) Prior Publication Data
US 2015/0031767 A1    Jan. 29, 2015

(30) Foreign Application Priority Data
Mar. 7, 2012    (ZA) .................................. 2012/01683

(51) Int. Cl.
| | |
|---|---|
| *A01N 43/16* | (2006.01) |
| *A01N 37/10* | (2006.01) |
| *A61K 31/194* | (2006.01) |
| *A61K 45/06* | (2006.01) |
| *A61K 31/352* | (2006.01) |
| *A61K 31/407* | (2006.01) |
| *A61K 38/12* | (2006.01) |

(52) U.S. Cl.
CPC ............. *A61K 31/194* (2013.01); *A61K 31/352* (2013.01); *A61K 31/407* (2013.01); *A61K 38/12* (2013.01); *A61K 45/06* (2013.01)

(58) Field of Classification Search
USPC .................................................. 514/454, 570
See application file for complete search history.

(56) References Cited

U.S. PATENT DOCUMENTS 6,569,900 B1 * 5/2003 Dekker et al. ................ 514/530

FOREIGN PATENT DOCUMENTS

WO    WO 2007125492 A2 * 11/2007
WO    WO 2009/147635 A1    12/2009

OTHER PUBLICATIONS

Hirsch et al (Journal of Antimicrobial Chemotherapy vol. 65 pp. 1119-1125 published 2010).*
Kumarasamy, K. et al., Lancet Infect Dis vol. 10, pp. 597-602. Published online Aug. 11, 2010.*
Producers of medicinal grade heavy metal free fulvic acid. FulHold: Efficacy—Anti-Bacterial, Jul. 24, 2011. Retrieved from the Internet Aug. 25, 2014: <http://web.archive.org/web/20110724004303/http://www.fulhold.com/index.php?id=96>.
Howsley, S. Determination of the in vitro efficacy of CHD-FA against multi-resistant enterobacteriaceae and mycobacteria. Fulhold: Final Report—EUPR_010_101101 v1, Jul. 24, 2011. Retrieved from the Internet Aug. 25, 2014: <http://web.archive.org/liveweb/http://www.fulhold.com/pics/Multi_Resistant_Enterobacteriaceae_and_Mycobacteria.pdf>.
International Search Report, mailed Jun. 19, 2013 in connection with PCT International Application No. PCT/IB2013/051772, filed Mar. 6, 2013.

* cited by examiner

*Primary Examiner* — Paul Zarek
*Assistant Examiner* — George W Kosturko
(74) *Attorney, Agent, or Firm* — John P. White; Cooper & Dunham LLP

(57) ABSTRACT

Fulvic acid as the active ingredient is used in the treatment or inhibition of multi-drug resistant bacteria, in particular NDM-1 bacteria producing carbapenemase or extended-spectrum β-lactamase (ES8L) resistant bacteria. The multi-drug resistant bacteria may be gram negative bacteria including, but not limited to, *Klebsiella pneumoniae* or *Escherichia coli*. The fulvic acid can be provided in combination with one or more antibiotics from the class of carbapenems or polymyxin antibiotics.

6 Claims, 2 Drawing Sheets

FULVIC ACID AND ANTIBIOTIC COMBINATION FOR THE INHIBITION OR TREATMENT OF MULTI-DRUG RESISTANT BACTERIA

CROSS-REFERENCE TO RELATED APPLICATIONS

This application is a §371 national stage of PCT International Application No. PCT/IB2013/051772, filed Mar. 6, 2013, claiming priority of South African Patent Application No. 2012/01683, filed Mar. 7, 2012, the contents of each of which are hereby incorporated by reference in their entirety.

BACKGROUND OF THE INVENTION

THIS invention relates to fulvic acid as the active ingredient for use in the treatment or inhibition of multi-drug resistant bacteria, in particular NDM-1 bacteria producing carbapenemase or extended-spectrum β-lactamase (ESBL) resistant bacteria. The invention further relates to fulvic acid as an active ingredient in combination with one or more antibiotics from the class of carbapenems or polymyxin antibiotics for use in the treatment of multi-drug resistant bacteria, in particular NDM-1 bacteria producing carbapenemase.

Fulvic acid is a fraction of the humic substances that are formed during the decay of plant and animal residues in the environment (MacCarthy at al., 1985) and that is soluble in water under all pH conditions. It is also generally of lower molecular size and weight and lower in colour intensity than humic acids also found in humic substances.

Typically, fulvic acids have been produced from bituminous coal using a controlled wet oxidation process (Bergh of al., 1997). These fulvic acids are referred to as oxifulvic acids. One such process for production of fulvic acids from coal was described in U.S. Pat. No. 4,912,256.

Such fulvic acids have been used in the treatment of inflammation, acne, eczema, and bacterial, fungal and viral infections such as described in International patent publication WO00/19999. Furthermore, U.S. Pat. Nos. 4,999,202 and 5,204,368 disclose compositions containing fulvic acid, salt or a derivative thereof, which have bacteriostatic or bacteriocidal properties and are useful as disinfectants.

However, fulvic acids derived from oxidation of coal contain high concentrations of heavy metals including aluminium, mercury, cadmium, chromium and lead that are now known to be harmful to humans and should be avoided in pharmaceutical preparations. International patent publication WO2007/125492 discloses a fulvic acid composition derived from a carbohydrate source by a process of wet oxidation and a method of producing such a composition. As a result of the carbohydrate starting material, the fulvic acid produced from this process contains a low content of these harmful elements. Such a composition is described as being useful for pharmaceutical application.

SUMMARY OF THE INVENTION

According to one aspect of the invention, there is provided fulvic acid, or a salt, ester or derivative thereof as the active ingredient for use in the treatment or inhibition of multi-drug resistant bacteria.

In particular, the multi-drug resistant bacteria are NDM-1 positive bacteria producing carbapenemase, or extended-spectrum β-lactamase (ESBL) resistant bacteria. For example, the multi-drug resistant bacteria may be gram negative bacteria including, but not limited to, *Klebsiella pneumoniae* or *Escherichia coil*.

According to a further aspect of the invention, there is provided a combination comprising fulvic acid, or a salt, ester or derivative thereof as an active ingredient together with one or more antibiotics from the class of carbapenems or polymyxin antibiotics for use in the treatment of multi-drug resistant bacteria.

In particular, the multi-drug resistant bacteria are NDM-1 positive bacteria producing carbapenemase. For example, the multi-drug resistant bacteria may be gram negative bacteria including, but not limited to, *Klebsiella pneumonia.*

Preferably, the carbapenem is selected from the group consisting of Meropenem, Ertapenem, Doripenem, Panipenem/Betamipron, and Biapenem.

Preferably, the polymyxin antibiotic is selected from the group consisting of colistin sulfate and colistimethate sodium (colistin methanesulfonate sodium, colistin sulfomethate sodium).

The fulvic acid, or a salt, ester or derivative thereof may have any pH, from acid to basic, although typically the pH is from acidic to neutral. The fulvic acid may be in the form of a solution buffered to a suitable pH. Preferably, the fulvic acid is either in the form of the acid or as a salt, for example a potassium salt.

The preferred fulvic acid is a carbohydrate derived fulvic acid (CHD-FA) such as that described in WO2007/125492. The fulvic acid described in this publication has a molecular weight not exceeding 20,000 Daltons, and a low content of the elements aluminium, mercury, cadmium, chromium and lead and is safe for pharmaceutical use in humans and animals. Preferably, the content of these elements does not exceed 20 ppm. The fulvic acid may be derived from a carbohydrate such as a saccharide. The preferred saccharide is sucrose, glucose or fructose.

The fulvic acid, or a salt, ester or derivative thereof or the combination may be formulated into a pharmaceutical dosage form, more particularly a liquid, tablet, capsule, cream, gel or other pharmaceutical dosage forms known to those skilled in the art.

According to a further aspect of the invention there is provided the use of the fulvic acid, or a salt, ester or derivative thereof or the combination according to the invention in the manufacture of a pharmaceutical composition for use in a method of treatment or inhibition of multi-drug resistant bacteria in a subject, the method comprising administration of the fulvic acid, or a salt, ester or derivative thereof, or the combination to the subject.

According to a further aspect of the invention there is provided a method of treating, killing, or inhibiting multi-drug resistant bacterial growth by the use of the fulvic acid, or a salt, ester or derivative thereof, or the combination of the invention.

In particular, the method of treating, killing, or inhibiting multi-drug resistant bacterial growth may be in a subject by administration of an effective amount of the fulvic acid, or a salt, ester or derivative thereof, or the combination of the invention to the subject.

The subject may be a human or non-human animal.

In particular, the multi-drug resistant bacteria are NDM-1 positive bacteria producing carbapenemase, or extended-spectrum β-lactamase (ESBL) resistant bacteria. For example, the multi-drug resistant bacteria may be gram negative bacteria including, but not limited to, *Klebsiella pneumoniae* or *Escherichia coli.*

The administration may be oral, intravenous, topical or any other suitable form of administration.

DESCRIPTION OF PREFERRED EMBODIMENTS

Figure 1:
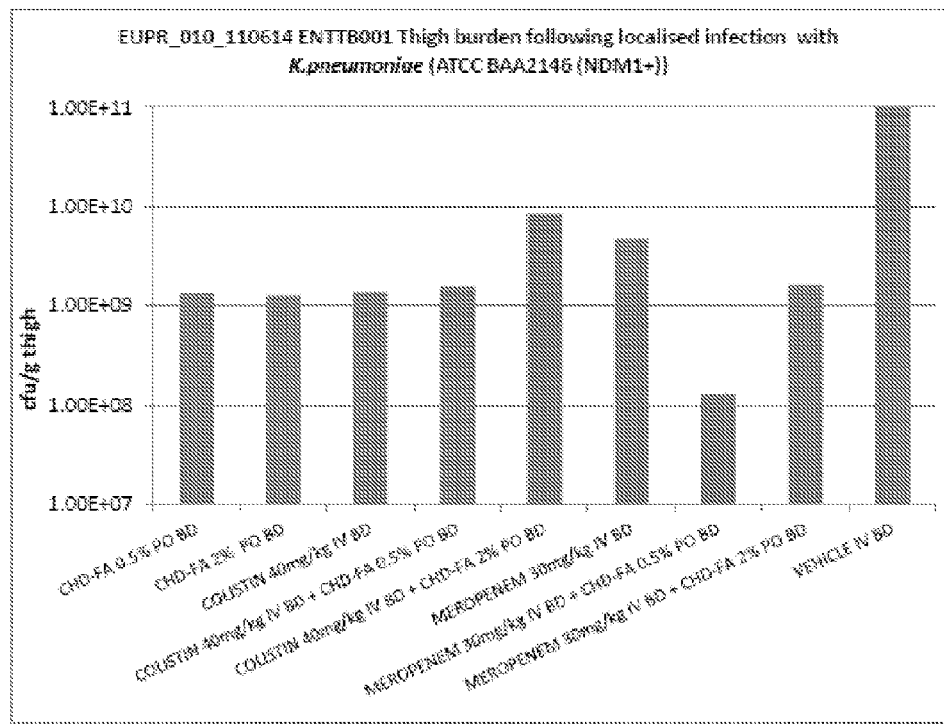
FIG. 1 Shows the mean thigh burden following infection with K. pneumonia (ATCC BAA2146, NDM-1+) in all treatment groups.

Fulvic acid as the active ingredient for use in the treatment of multi-drug resistant bacteria, in particular NDM-1 bacteria producing carbapenemase or extended-spectrum β-lactamase (ESBL) resistant bacteria is herein described. In addition, fulvic acid as an active ingredient in combination with one or more antibiotics from the class of carbapenems or polymyxin antibiotics for use in the treatment of multi-drug resistant bacteria, in particular NDM-1 bacteria producing carbapenemase, is described.

New Delhi metallo-beta-lactamase-1 (or NDM-1) was first detected in a Klebsiella pneumoniae isolate in 2008. However, it was later detected in bacteria around the world, including in India, Pakistan, the United Kingdom, North America, Japan and Brazil. Generally, the enzyme is produced by Gram-negative bacteria such as Escherichia coil, Acinetobacter and Klebsiella, but the NDM-1 gene can spread by horizontal gene transfer between different strains of bacteria, thereby spreading the incidence of resistant infections. Gram-negative bacteria in particular are promiscuous with their exchange of DNA fragments and so resistance such as NDM-1 can spread widely through the gram negative bacterial population.

Extended-spectrum β-lactamases (ESBLs) are beta-lactamases that hydrolyze extended-spectrum cephalosporins such as cefotaxime, ceftriaxone, ceftazidime and oxyimino-monobactam aztreonam, all with an oxyimino side chain.

NDM-1 is an enzyme that makes bacteria resistant to a broad range of beta-lactam antibiotics, such as the antibiotics of the carbapenem family. For example, carbapenems include Meropenem, Ertapenem, Doripenem, Panipenem/betamipron, and Biapenem. Unfortunately, these antibiotics are presently the mainstay for the treatment of antibiotic-resistant bacterial infections and so this resistance gene is a cause for great concern. The NDM-1 protein belongs to a large family of beta-lactamase enzymes, the carbapenemases, and infections by bacteria producing carbapenemases are very difficult to treat since there are almost no new compounds that will work against these multi-drug-resistant bacteria. Furthermore, due to the desire to avoid development of generalized resistance and the fact that, in general, carbapenems have poor oral bioavailability, they are selectively administered intravenously in the hospital setting.

An alternative antibiotic to the carbapenems that has been used successfully against multi-drug resistant carbapenemase producing bacteria is Colistin. Colistin (or polymyxin E) is an antibiotic produced by certain strains of Bacillus polymyxa var. colistinus. It is also a last-resort antibiotic for multidrug-resistant bacteria such as Klebsiella, Pseudomonas aeruginosa, and Acinetobacter, but unfortunately resistance to Colistin has also been identified. Colistin also is not absorbed via the gastrointestinal tract and therefore must be given intravenously. Furthermore, the dosing is complicated.

Therefore, an alternative effective agent which can be used orally would be highly advantageous.

The fulvic acid was that described in, and produced by the method described in WO 2007/125492 and is hereinafter referred to as CHD-FA.

In the first study described herein, the antibacterial efficacy of fulvic acid against a number of multi-drug resistant bacterial strains was assessed.

The second study assessed the the antibacterial efficacy of fulvic acid together with antibiotics from the carbapenem family against a NDM-1 multi-drug resistant bacterial strain.

The following examples are for the purpose of illustration only and are not to be construed as limiting on the invention in any way.

EXAMPLE 1

Antibacterial Activity Against Multi-Resistant Bacteria of Fulvic Acid

Summary

The in vitro efficacy of CHD-FA for activity against multi-resistant Enterobactenaceae was assessed. The CHD-FA active ingredient was stored in the dark at room temperature following delivery.

Methods a) Strains

Susceptibility tests were performed on a range of multi-drug resistant Enterobactenaceae strains. Details of the strains used are outlined in table 1.

b) Revival and Growth of the Strains

All strains were recovered from long-term storage at −80° C. by sub-culturing onto Cled agar plates. Plates were then incubated in air at 35-37° C. for 24 hours. Following visual checks to ensure purity and appropriate colony characteristics, isolates were deemed suitable for use.

TABLE 1

NDM-1 and KPC containing Enterobacteriaceae strains (study 1)

| SPECIES | Number | STRAIN | COMMENTS |
|---|---|---|---|
| Klebsiella pneumoniae | ATCC BAA 2146 | New Delhi metallo-beta-lactamase (NDM-1) positive | $bla_{KPC}$ −ve by PCR $bla_{NDM}$ +ve by PCR |
| Klebsiella pneumoniae | NCTC1 3443 | New Delhi metallo-beta-lactamase (NDM-1) positive | N/A |
| Klebsiella pneumoniae | ATCC BAA 1705 | Modified Hodge Test (MHT) positive control designation | Strain produces K. pneumoniae carbapenemase (KPC) $blaj_{KPC}$ +ve by PCR |

TABLE 1-continued

NDM-1 and KPC containing Enterobacteriaceae strains (study 1)

| SPECIES | Number | STRAIN | COMMENTS |
|---|---|---|---|
| Klebsiella pneumoniae | ATCC 700603 | ESBL control strain | produces beta-lactamase SHV-18 |
| Escherichia coli | Clinical 7 | Clinical strain | ESBL Multi resistant strain |
| Escherichia coli | ATCC 25922 | CLSI control strain | Susceptible isolate | c) Preparation of the Inoculum

The inocula for each strain were prepared by picking 5-10 distinct colonies from the culture plates and suspending them in 3 ml of sterile saline. The inoculum was resuspended by vigorous shaking on a vortex mixer for 15 seconds. The turbidity was then adjusted to McFarland standard 0.5 (1-5×$10^6$ CFU/mL.). The inoculum was further diluted in Mueller Hinton broth for MIC tests to give a final inoculum in each well of 2-8×$10^5$ CFU/ml.

d) MIC Assay Conditions

MICs were tested in Mueller Hinton broth in accordance with the appropriate CLSI guidelines.

STEP 1: Addition of Test Article a. The stock solution was provided as a 4% stock solution. This was further diluted in the appropriate media (Mueller Hinton broth) to give a top starting concentration of 2% in the assay. In addition, for each strain, a comparator control was included. The final concentration range for the comparator control (ciprofloxacin) was 0.03-16 mg/L. 100 µL of Mueller Hinton broth was dispensed into each well in columns 2-12. 200 µL of the appropriate test compound solution (at 4%) was dispensed into each well in column 1.

b. 100 µL aliquots were pipetted from column 1 wells and dispensed into column 2 with a multichannel pipette (±2% coefficient of variation) thus diluting two-fold.

100 µL samples were then pipetted from column 2 wells and dispensed into column 3. The process was repeated through to column 10. The final 100 µL of diluted drug from column 10 was then discarded. Row 11 acted as a positive control (no drug or test article, organisms added), Row 12 acted as a negative control (no drug or test article, and no organisms added).

STEP 2: Addition of Bacterial Strains

100 µL of the appropriate inoculum suspension in Mueller Hinton broth was added to the appropriate wells. This resulted in a well containing 200 µL final volume (made up of 100 µL diluted compound or diluents and 100 µL of inoculum or broth alone).

STEP 3: Incubation of Assay Plates

All plates were incubated in the dark at 35-37° C. in air for 18-24 hours.

STEP 4: Reading of Plates

Plates were read visually and spectrophotometrically (450 nm) where possible, 20 or 72 hours post inoculation, Endpoints of 50%>, 80%> and 100%> inhibition were determined (or CLSI interpretation endpoints following visual examination).

Results a) Visual MIC Values (50%, 80% and 100% Inhibition)

The CHD-FA alone was effective against NDM-1, KPC and ESBL positive K. pneumonia and multi-drug resistant E. coli strains with a 100% MIC value of only 0.06-0.12% CHD-FA as shown in Table 2.

This compares favourably against ciprofloxacin which was not effective against either NDM-1, nor KPC positive K. pneumonia strains, having an MIC of more than 16 µg/ml. CHD-FA alone was as effective as ciprofloxacin against K. pneumonia and E. coli ESBL positive strains.

TABLE 2

MIC efficacy data of CHD-FA against various Enterobacteriaceae strains

| | K. pneumoniae ATCC BAA 2146 | | | K. pneumonia NCTC 13443 | | | K. pneumoniae ATCC BAA 1705 | | |
|---|---|---|---|---|---|---|---|---|---|
| Compound | 100% | 80% | 50% | 100% | 80% | 50% | 100% | 80% | 50% |
| CHD-FA (%) | 0.12 | 0.12 | 0.12 | 0.06 | 0.06 | 0.06 | 0.06 | 0.06 | 0.06 |
| Ciprofloxacin (µg/ml) | >16 | >16 | >16 | >16 | >16 | >16 | >16 | >16 | >16 |

| | K. pneumonia ATCC700603 | | | E. coli Clinical strain 7 | | | E. coli ATCC 25922 | | |
|---|---|---|---|---|---|---|---|---|---|
| Compound | 100% | 80% | 50% | 100% | 80% | 50% | 100% | 80% | 50% |
| CHD-FA (%) | 0.06 | 0.06 | 0.06 | 0.06 | 0.06 | 0.06 | 0.06 | 0.06 | 0.06 |
| Ciprofloxacin (µg/ml) | 0.25 | 0.25 | 0.25 | 0.06 | 0.06 | 0.06 | ≤0.03 | ≤0.03 | ≤0.03 |

Summary

CHD-FA was highly effective against multi-drug resistant Gram negative bacilli including NDM-1 positive strains with all organisms being 100% inhibited using a concentration of ≤112% CHD-FA.

EXAMPLE 2

Efficacy of CHD-FA Alone or in Combination with a Carbapenem Antibiotic in a Mouse Thigh Model of *K. pneumonia* Infection Methods a) Regulatory All animal experiments were performed under UK Home Office Licence with local ethical committee clearance. All experiments were performed by technicians that have completed parts 1, 2 and 3 of the Home Office Personal License course and hold current personal licenses.

b) Mouse Strain

Mice used in this study were supplied by Charles River UK and were specific pathogen free. The strain of mouse used was CD1, which is a well characterized outbred strain. Mice were 16-18 g on receipt at Euprotec's facility and were allowed to acclimatize for 7 days (target weight at the start of the experiment 22-25 g).

c) Animal Housing

Mice were housed in sterile individual ventilated cages exposing mice at all times to HEPA filtered sterile air (http://www.tecniplast.it/_assets/panorama/Panorama30.pdf). Mice had free access to food and water (sterile) and had sterile aspen chip bedding (changed every 3-4 days or as appropriate). The room temperature was 22° C.±1° C., with a relative humidity of 50-60% and maximum background noise of 56 dB. Mice were exposed to 12 hour light/dark cycles with dawn/dusk phases.

d) *Klebsiella pneumoniae* Isolate

*Klebsiella pneumoniae* (ATCC BAA2146 NDM-1+ ($bla_{ndm}$) was used throughout the study.

Experimental Design a) Experimental Group Size

In this study, 6 mice were used in each treatment group.

b) Immunosuppression

Mice were rendered temporarily neutropenic by immunosuppression with cyclophosphamide at 150 mg/kg four days before infection and 100 mg/kg one day before infection by intraperitoneal injection. The immunosuppression regime leads to neutropenia starting 24 hours post administration which continues throughout the study.

c) Infection 24 hours post the second round of immunosuppression mice were infected with *K. pneumoniae* intramuscularly into both lateral thigh muscles using 2.5×10 cfu/mouse thigh.

d) Antibacterial Therapy

Antibacterial treatment was initiated 2 hours post infection (Table 3) and was administered twice (exactly 12 hours apart). An aliquot of 4% CHD-FA stock solution as adjusted to pH 5 with 10 M sodium hydroxide solution then diluted either 1:2 or 1:8 with 0.9% saline to give a dosing solution of 2% (200 mg/kg) and 0.5% (50 mg/kg) CHD-FA respectively.

Colistin was diluted in 0.9% saline to give a dosing solution of 4 mg/ml (40 mg/kg). Meropenem was diluted in 0.9% saline to give a dosing solution of 3 mg/ml (30 mg/kg). The vehicle was 0.9% saline. Following reconstitution, the suspensions were vortexed to ensure complete dissolution.

CHD-FA was administered by gavage, whereas Colistin, Meropenem and the vehicle were administered IV at 10 ml/kg (requiring individual mice to be administered ~0.25 ml/dose).

e) Endpoints 24 hours post infection, the clinical condition of all animals was assessed prior to them being humanely euthanized. Animal weight was determined before both thighs were removed and weighed individually. Individual thigh tissue samples were homogenized in ice cold sterile phosphate buffered saline. Thigh homogenates were then quantitatively cultured on to CLED agar and incubated at 37° C. for 24 hrs and colonies counted daily.

f) Statistical Analysis

Quantitative thigh tissue burden data for CHD-FA were analysed using the statistical test Kruskal Wallis test (corrected for multiple comparisons) and compared to Colistin, Meropenem and vehicle monotherapy, plus Colistin/CHD-FA and Meropenem/CHD-FA combinations.

TABLE 3

| | | | Experimental Treatment Groups | | | |
|---|---|---|---|---|---|---|
| Box number | Treatment | Dose | Frequency | 1$^{st}$ Dose | 2$^{nd}$ Dose | Route |
| 1 | CHD-FA | 0.5% | 2 X daily | 2 h | 14 h | Oral |
| 2 | CHD-FA | 2% | 2 X daily | 2 h | 14 h | Oral |
| 3 | Colistin | 40 mg/kg | 2 X daily | 2 h | 14 h | IV |
| 4 | Colistin + CHD-FA | 40 mg/kg + 0.5% | 2 X daily | 2 h | 14 h | IV/Oral |
| 5 | Colistin + CHD-FA | 40 mg/kg + 2% | 2 X daily | 2 h | 14 h | IV/Oral |
| 6 | Meropenem | 30 mg/kg | 2 X daily | 2 h | 14 h | IV |
| 7 | Meropenem + CHD-FA | 30 mg/kg + 0.5% | 2 X daily | 2 h | 14 h | IV/Oral |
| 8 | Meropenem + CHD-FA | 30 mg/kg + 2% | 2 X daily | 2 h | 14 h | IV/Oral |
| 9 | Vehicle | — | 2 X daily | 2 h | 14 h | IV |

Results a) In viva Efficacy

A severe model of *K. pneumoniae* thigh infection was successfully established with ~11 log 10 cfu/g in thighs of vehicle control mice 24 hrs post infection. Moderate signs of infection were observed in vehicle treated mice. Treatment with all test articles were well tolerated during the study with no adverse effects observed.

Quantitative thigh tissue burden data indicated that all treatment groups demonstrated statistically significant reduction in thigh burdens compared with vehicle only treated mice (1.48-3.3 log 10 reduction, P<0.0001 for all treatment groups except Colistin 40 mg/kg+CHD-FA 2%, P=0.0102 (StatsDirect-Kruskal-Wallis: all pairwise comparisons (Conover-Inman)).

Remarkably CHD-FA monotherapy administered at 2% and 0.5% (200 and 50 mg/kg) was as effective as 40 mg/kg Colistin or 30 mg/kg Meropenem at reducing the tissue burden.

The greatest reduction in burden was observed with the combination treatment group Meropenem 30 mg/kg+CHD-FA 0.5%, IV+PO BD (3.3 log 10 reduction, P<0.0001).

The reduction in burden following CHD-FA treatment at 0.5% and 2% PO BD was not statistically different to that observed with either Colistin 40 mg/kg IV BD or Meropenem 30 mg/kg IV BD monotherapy. However, data demonstrates significantly improved efficacy when CHD-FA 5% is administered in combination with Meropenem, rather than alone (P=0.0008).

The rank efficacy order of efficacy compared with vehicle control group was as follows:
1. Meropenem 30 mg/kg+CHD-FA 0.5%, IV+PO BD (3.3 log 10 reduction, P<0.0001),
2. CHD-FA 2%, PO BD (2.31 log 10 reduction, P<0.0001),
3. CHD-FA 0.5%, PO BD (2.28 log 10 reduction, P<0.0001),
4. Colistin 40 mg/kg, IV BD (2.27 log 10 reduction, P<0.0001),
5. Colistin 40 mg/kg+CHD-FA 0.5%, IV+PO BD (2.21 log 10 reduction, P<0.0001),
6. Meropenem 30 mg/kg+CHD-FA2%, IV+PO BD (2.20 log 10 reduction, P<0.0001),
7. Colistin 40 mg/kg+CHD-FA 2%, IV+PO BD (2.20 log 10 reduction, P<0.0102), and
8. Meropenem 30 mg/kg, IV BD (1.74 log 10 reduction, P<0.0001).

Table 4 sets out a summary of the thigh tissue burden in the test mice with and without treatment.

TABLE 4

Thigh tissue burden summary table.

| Group | Treatment | Group Average (cfu/g) | Group Ave. Log 10 cfu/g | Log reduction from vehicle | n = | No. Sterilised* |
|---|---|---|---|---|---|---|
| 1 | CHD-FA 0.5%, oral 2X daily | 1358950384 | 9.13 | 2.28 | 12 | 0 |
| 2 | CHD-FA 2%, oral 2X daily | 1272314925 | 9.10 | 2.31 | 12 | 0 |
| 3 | Colistin 40 mg/kg, IV 2X daily | 1388363808 | 9.14 | 2.27 | 12 | 0 |
| 4 | Colistin 40 mg/kg + CHD-FA 0.5%, IV + oral 2X daily | 1570868780 | 9.20 | 2.21 | 12 | 0 |
| 5 | Colistin 40 mg/kg + CHD-FA 2%, IV + oral 2X daily | 8468797243 | 9.93 | 1.48 | 12 | 0 |
| 6 | Meropenem 30 mg/kg, IV 2X daily | 4729505542 | 9.67 | 1.74 | 12 | 0 |
| 7 | Meropenem 30 mg/kg + CHD-FA 0.5%, IV + oral 2X daily | 129247657 | 8.11 | 3.30 | 12 | 0 |
| 8 | Meropenem 30 mg/kg + CHD-FA 2%, IV + oral 2X daily | 1624414808 | 9.21 | 2.20 | 12 | 0 |
| 9 | Vehicle | 257564729875 | 11.41 | 0.00 | 12 | 0 |

*5 or less colonies detected on neat plate

TABLE 5

Kruskal-Wallis statistical tests (corrected for multiple comparisons) of test articles CHD-FA, Colistin and Meropenem in temporarily neutropenic mice infected with *Klebsiella pneumoniae* (ATCC BAA2146 (NDM-1[+]) intramuscularly.

| | CHD-FA 0.5%, PO BD | CHD-FA 2%, PO BD | Colistin 40 mg/kg, IV BD | Colistin 40 mg/kg + CHD-FA 0.5%, IV + PO BD | Colistin 40 mg/kg + CHD-FA 2%, IV + PO BD |
|---|---|---|---|---|---|
| CHD-FA 0.5%, PO BD | | NS | NS | NS | P = 0.0017 |
| CHD-FA 2%, PO BD | | | NS | NS | P = 0.0012 |
| Colistin 40 mg/kg, IV BD | | | | NS | P = 0.0008 |
| Colistin 40 mg/kg + CHD-FA 0.5%, IV + PO BD | | | | | P = 0.0011 |
| Colistin 40 mg/kg + CHD-FA 2%, IV + PO BD | | | | | |
| Meropenem 30 mg/kg, IV BD | | | | | |
| Meropenem 30 mg/kg + CHD-FA 0.5%, IV + PO BD | | | | | |
| Meropenem 30 mg/kg + CHD-FA 2%, IV + PO BD | | | | | |
| Vehicle | | | | | |

TABLE 5-continued

Kruskal-Wallis statistical tests (corrected for multiple comparisons) of test articles CHD-FA, Colistin and Meropenem in temporarily neutropenic mice infected with *Klebsiella pneumoniae* (ATCC BAA2146 (NDM-1$^+$) intramuscularly.

| | Meropenem 30 mg/kg, IV BD | Meropenem 30 mg/kg + CHD-FA 0.5%, IV + PO BD | Meropenem 30 mg/kg + CHD-FA 2%, IV + PO BD | Vehicle |
|---|---|---|---|---|
| CHD-FA 0.5%, PO BD | NS | P = 0.0008 | NS | P < 0.0001 |
| CHD-FA 2%, PO BD | NS | P = 0.0011 | NS | P < 0.0001 |
| Colistin 40 mg/kg, IV BD | NS | P = 0.0018 | NS | P < 0.0001 |
| Colistin 40 mg/kg + CHD-FA 0.5%, IV + PO BD | NS | P = 0.0013 | NS | P < 0.0001 |
| Colistin 40 mg/kg + CHD-FA 2%, IV + PO BD | NS | P < 0.0001 | p = 0.0044 | P = 0.0102 |
| Meropenem 30 mg/kg, IV BD | | P < 0.0001 | NS | P < 0.0001 |
| Meropenem 30 mg/kg + CHD-FA 0.5%, IV + PO BD | | | P = 0.0003 | P < 0.0001 |
| Meropenem 30 mg/kg + CHD-FA 2%, IV + PO BD | | | | P < 0.0001 |
| Vehicle | | | | |

NS: Not statistically significant

Figure 2:
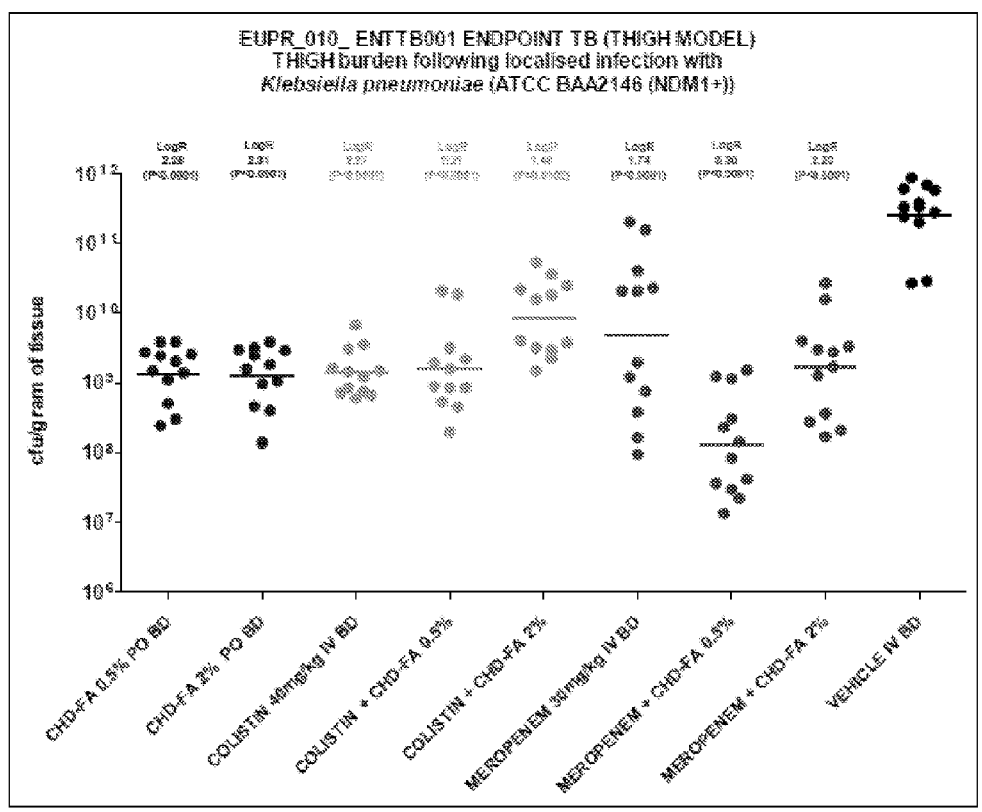
FIG. 2 Shows a scattergram of the thigh burden following infection with K. pneumonia (ATCC BAA2146, NDM-1+) in all treatment groups.

FIG. 1 sets out the mean thigh burden following infection with *K. pneumonia* (ATCC BAA2146, NDM-1$^+$) and all treatment groups. FIG. 2 sets out a scattergram of the thigh burden following infection with *K. pneumonia* (ATCC BAA2146, NDM-1$^+$) and all treatment groups. The geometric mean burden of each treatment is indicated by a horizontal bar. Above each column the log 10 reduction of that treatment group compared to the vehicle group is recorded.

Summary

The aim of the study was to assess the efficacy of CHD-FA administered as a monotherapy or as combination therapy with either Colistin or Meropenem in a neutropenic murine thigh infection model caused by a multi-drug resistant strain of *Klebsiella pneumoniae* (New Delhi metallo-beta-lactamase or NDM-1 positive). Efficacy was compared using tissue burdens from the thigh at the end of the experiment. Treatment was initiated 2 hours post-infection, and administered twice exactly 12 hours apart. Mice were euthanized 24 hours post infection.

A severe infection caused by *K. pneumoniae* was established in the thighs of vehicle treated mice 24 hrs post infection. However, despite this high level of infection no mice succumbed to infection prior to the end of the study, although moderate signs of infection (local tenderness) were observed.

Quantitative thigh tissue burden data indicated that all treatment groups demonstrated highly statistically significant reduction in thigh burdens compared with vehicle only treated mice.

Remarkably CHD-FA monotherapy administered at 2% and 0.5% (0.2 and 0.05 mg/kg) was as effective as 40 mg/kg Colistin or 30 mg/kg Meropenem at reducing the tissue burden.

The greatest reduction in thigh burden was observed following treatment with the combination of Meropenem 30 mg/kg CHD-FA 0.5% highlighting the fact that not only was CHD-FA effective as monotherapy but it also augmented the treatment efficacy of the currently used drugs in a synergistic manner.

Conclusion

CHD-FA administered either as a monotherapy or as a combination therapy with either Colistin or Meropenem exhibited highly significant efficacy against multi-drug resistant *Klebsiella pneumoniae* in a localised thigh infection model. Combination therapy with 30 mg/kg Meropenem plus 50 mg/kg CHD-FA showed superior efficacy compared to the same dose of CHD-FA, Meropenem or Colistin administered as a monotherapy.

REFERENCES

Bergh J. J., Cronje I. J., Dekker J., Dekker T. G., Gerritsma L. M.& Mienie L. J. 1997. Non-catalytic oxidation of water-slurried coal with oxygen: identification of fulvic acids and acute toxicity. Fuel 76, 149-154 (1997).

MacCarthy P, Clapp C E, Malcolm R L, Bloom P R. Humic substances in soil and crop sciences: selected readings. Proceedings of a symposium by International Humic Substances Society, Soil Science Society of America, American Society of Agronomy and Crop Science Society of America, Chicago, Ill., 2 Dec. 1985.

The invention claimed is:

1. A method of treating, killing or inhibiting growth of multi-drug resistant bacteria in a subject, wherein said multi-drug resistant bacteria are gram negative bacteria and positive for NDM-1 producing carbapenemase; said method comprising administering to the subject an amount of a composition comprising carbohydrate-derived fulvic acid (CHD-FA) or a salt thereof, as an active ingredient together with meropenem so as to treat, kill or inhibit growth of such bacteria in the subject.

2. A method of claim 1, wherein the gram negative bacteria are *Klebsiella pneumonia* or *Escherichia coli*.

3. A method of claim 1, wherein the fulvic acid, or a salt thereof, has a pH which is acidic or neutral.

4. A method of claim 1, wherein the composition is formulated into a pharmaceutical dosage form.

5. A method of claim 4, wherein the pharmaceutical dosage form is a liquid, tablet, capsule, cream, gel or other pharmaceutical dosage forms known to those skilled in the art.

6. A method of claim 1, wherein the subject is a human or non-human animal.

* * * * *